US 9,488,565 B2

(12) United States Patent
Zielinski et al.

(10) Patent No.: US 9,488,565 B2
(45) Date of Patent: Nov. 8, 2016

(54) METHOD AND APPARATUS FOR DETECTING MOISTURE IN PORTABLE ELECTRONIC DEVICES

(71) Applicant: Revive Electronics, LLC, Fishers, IN (US)

(72) Inventors: Reuben Quincey Zielinski, Fishers, IN (US); Joel Christopher Trusty, Fishers, IN (US)

(73) Assignee: Revive Electronics, LLC, Carmel (IN)

( * ) Notice: Subject to any disclaimer, the term of this patent is extended or adjusted under 35 U.S.C. 154(b) by 132 days.

(21) Appl. No.: 14/080,705

(22) Filed: Nov. 14, 2013

(65) Prior Publication Data
US 2014/0260543 A1    Sep. 18, 2014

Related U.S. Application Data

(60) Provisional application No. 61/726,151, filed on Nov. 14, 2012.

(51) Int. Cl.
G01N 19/10  (2006.01)
G01N 27/04  (2006.01)
G01N 1/24   (2006.01)

(52) U.S. Cl.
CPC ............ *G01N 19/10* (2013.01); *G01N 27/048* (2013.01); *G01N 1/24* (2013.01)

(58) Field of Classification Search
CPC ...... G01N 19/10; G01N 1/24; G01N 27/048; G01N 1/2226
See application file for complete search history.

(56) References Cited

U.S. PATENT DOCUMENTS
2,496,054 A    1/1950   Hoyler
2,846,710 A    8/1958   Haka
(Continued)

FOREIGN PATENT DOCUMENTS
CN    2065321 U    11/1990
CN    201018665    2/2008
(Continued)

OTHER PUBLICATIONS

International Search Report and Written Opinion issued in PCT/US2013/070178. Feb. 24, 2014.
International Search Report and Written Opinion issued in PCT/US2013/024277, pp. 1-16 May 5, 2013.
"How to Dry Out a Wet Cell Phone," ehow.com, http://www.ehow.com/print/how_2042819_dry-out-wet-cell-phone.html, pp. 1-2. Jun. 5, 2013 (obtained from PTO-892 form mailed by US Patent Office on Jun. 16, 2012 with respect to U.S. Appl. No. 12/459,700, which was retrieved on Dec. 8, 2011).
(Continued)

*Primary Examiner* — Daniel S Larkin
*Assistant Examiner* — Jamar Ray
(74) *Attorney, Agent, or Firm* — Baker & McKenzie LLP (57) ABSTRACT

The present invention provides a unique method and apparatus for the automatic detection of water in portable electronic devices, such as cell phones, digital music players, pagers, cameras, tablet computers and the like, after these units have been subjected to water, high-humidity conditions, or other unintended deleterious wetting agents that could render such devices inoperable. Such detection can be performed without any disassembly of the device required. At least one embodiment provides a user-controlled vacuum plenum that simultaneously scavenges air from within the portable electronic device while sampling the relative humidity to determine the level of water or moisture within the device. The relative humidity is sampled by a microcontroller and displayed on a user friendly interface to allow repair and retail shops to quickly determine whether the portable electronic device contains water or moisture within its enclosed interior.

22 Claims, 6 Drawing Sheets

(56) References Cited

U.S. PATENT DOCUMENTS

| | | |
|---|---|---|
| 3,897,604 A | 8/1975 | Weimer |
| 3,932,944 A | 1/1976 | Chiba |
| 4,020,563 A | 5/1977 | Hoefer |
| 4,386,471 A | 6/1983 | Bowrey et al. |
| 4,589,971 A | 5/1986 | Mayeaux |
| 4,704,805 A | 11/1987 | Kaya et al. |
| 4,733,428 A | 3/1988 | Malinge et al. |
| 4,882,851 A | 11/1989 | Wennerstrum et al. |
| 5,005,410 A | 4/1991 | Webster et al. |
| 5,067,251 A | 11/1991 | Zlobinsky et al. |
| 5,293,697 A | 3/1994 | Kawakami |
| 5,318,164 A | 6/1994 | Barnes et al. |
| 5,335,703 A | 8/1994 | deJong |
| 5,343,747 A | 9/1994 | Rosen |
| 5,349,845 A | 9/1994 | Blom |
| 5,456,025 A | 10/1995 | Joiner et al. |
| 5,578,753 A | 11/1996 | Weiss et al. |
| 5,625,962 A | 5/1997 | Fleissner |
| 5,671,546 A | 9/1997 | Haala |
| 5,852,879 A | 12/1998 | Schumaier |
| 5,889,466 A | 3/1999 | Ferguson |
| 5,992,049 A | 11/1999 | Trost |
| 6,025,580 A | 2/2000 | Yagi |
| 6,039,696 A | 3/2000 | Bell |
| 6,122,836 A | 9/2000 | Tenedini et al. |
| 6,399,920 B1 | 6/2002 | Guinn |
| 6,551,552 B1 | 4/2003 | Lyublinski et al. |
| 6,557,268 B1 | 5/2003 | Berg et al. |
| 6,568,249 B2 | 5/2003 | Devine |
| 6,622,399 B1 | 9/2003 | Theriault et al. |
| 6,675,636 B2 | 1/2004 | Sadler |
| 6,821,025 B2 | 11/2004 | Gerhard |
| 6,834,443 B2 | 12/2004 | Bloemendaal |
| 6,893,530 B2 | 5/2005 | Kishimoto et al. |
| 6,938,359 B2 | 9/2005 | Birgersson et al. |
| 7,050,837 B2 | 5/2006 | Menz et al. |
| 7,194,822 B2 | 3/2007 | Kolari |
| 7,205,900 B2 | 4/2007 | Liu et al. |
| 7,243,857 B2 | 7/2007 | Kallestad |
| 7,460,350 B2 | 12/2008 | Talbot et al. |
| 7,557,466 B2 | 7/2009 | Wong et al. |
| 7,594,343 B2 | 9/2009 | Woerdehoff et al. |
| 7,612,315 B2 | 11/2009 | Corradini |
| 7,631,538 B2 | 12/2009 | Imhof |
| 7,665,226 B2 | 2/2010 | Tsuruta et al. |
| 7,814,678 B2 | 10/2010 | Romanek |
| 8,058,588 B2 | 11/2011 | Gagas et al. |
| 8,108,074 B2 | 1/2012 | Boder |
| 8,112,900 B2 | 2/2012 | Romanek |
| 8,203,689 B2 | 6/2012 | Gomi |
| 8,281,499 B2 | 10/2012 | Friesen et al. |
| 8,355,233 B2 | 1/2013 | Schumacher et al. |
| 8,416,542 B2 | 4/2013 | Nakamura |
| 8,446,049 B2 | 5/2013 | Lee |
| 8,498,087 B2 | 7/2013 | Rabu et al. |
| 2001/0045421 A1 | 11/2001 | Sullivan |
| 2003/0019124 A1 | 1/2003 | Miyakawa et al. |
| 2003/0115768 A1 | 6/2003 | Hoffman |
| 2004/0050076 A1 | 3/2004 | Palfy et al. |
| 2004/0079136 A1 | 4/2004 | Pillion |
| 2005/0079888 A1 | 4/2005 | Menz et al. |
| 2005/0218239 A1 | 10/2005 | Busch |
| 2006/0058069 A1 | 3/2006 | Garcia et al. |
| 2006/0208914 A1 | 9/2006 | Liu et al. |
| 2006/0255166 A1 | 11/2006 | Imamura et al. |
| 2007/0258870 A1 | 11/2007 | Brown et al. |
| 2008/0281528 A1* | 11/2008 | Relle, Jr. ............... G01N 1/2273 702/19 |
| 2009/0019718 A1 | 1/2009 | Mittleman et al. |
| 2009/0145783 A1 | 6/2009 | Forker |
| 2009/0158614 A1 | 6/2009 | Singh et al. |
| 2009/0272176 A1 | 11/2009 | Lopez et al. |
| 2009/0273480 A1 | 11/2009 | Mittleman et al. |
| 2010/0032600 A1* | 2/2010 | Doe ...................... F16K 27/003 251/129.15 |
| 2010/0095504 A1 | 4/2010 | Slack et al. |
| 2010/0103566 A1 | 4/2010 | Chen |
| 2010/0122470 A1 | 5/2010 | Davis et al. |
| 2010/0273477 A1* | 10/2010 | Namaky ............... H04L 67/125 455/426.1 |
| 2011/0047814 A1 | 3/2011 | Watson et al. |
| 2011/0067262 A1 | 3/2011 | Eero |
| 2011/0099831 A1 | 5/2011 | Parisi et al. |
| 2011/0137607 A1 | 6/2011 | Hsieh |
| 2012/0020015 A1 | 1/2012 | Tian et al. |
| 2012/0038374 A1 | 2/2012 | Johnson |
| 2012/0085324 A1 | 4/2012 | Saito et al. |
| 2012/0171462 A1 | 7/2012 | Tsai |
| 2012/0304483 A1 | 12/2012 | Sirard et al. |
| 2013/0088094 A1 | 4/2013 | Paik |
| 2013/0096375 A1 | 4/2013 | Iyama et al. |
| 2013/0111227 A1 | 5/2013 | Sauerwein, Jr. |
| 2013/0167874 A1 | 7/2013 | Mittleman et al. |
| 2013/0182360 A1 | 7/2013 | Stevens et al. |

FOREIGN PATENT DOCUMENTS

| | | |
|---|---|---|
| CN | 101986360 | 3/2011 |
| CN | 201955259 U | 8/2011 |
| EP | 0539607 | 5/1993 |
| EP | 1125177 | 1/2004 |
| JP | 2001197175 A | 7/2001 |
| JP | 2011171894 | 9/2011 |
| WO | 0023861 | 4/2000 |
| WO | 0053983 | 9/2000 |
| WO | 2007033493 | 3/2007 |
| WO | 2009087102 | 7/2009 |
| WO | 2010070551 | 6/2010 |

OTHER PUBLICATIONS

U.S. Trademark Registration No. 4,280,438 for the mark Drybox Jan. 22, 2013.
Exhibitor News from International CTIA Wireless 2012 May 3, 2013.
Lucio, Valentino, "A Solution for Soaked Cells," San Antonio Express-News, pp. 1-3 Oct. 19, 2011.
Cooper, Sean, "Drybox Rescue Station: the ultimate cellphone drying system (hands-on)," www.engadget.com, pp. 1-13 May 22, 2013.
Drybox The New Way to Save a Wet Phone Fast, http://www.dryboxrescue.com/, pp. 1-5 Jun. 26, 2013.
International Preliminary Report on Patentability issued in PCT/US2013/024277, pp. 1-12 Aug. 14, 2014.
Non-Final Rejection issued in U.S. Appl. No. 13/756,879. Sep. 20, 2013.
Response After Non-Final Action filed in U.S. Appl. No. 13/756,879. Dec. 20, 2013.
Final Rejection issued in U.S. Appl. No. 13/756,879. Feb. 28, 2014.
Response After Final Action filed in U.S. Appl. No. 13/756,879. May 28, 2014.
Response After Final Action filed in U.S. Appl. No. 13/756,879. Jun. 13, 2014.
Advisory Action issued in U.S. Appl. No. 13/756,879. Jun. 18, 2014.
Advisory Action issued in U.S. Appl. No. 13/756,879. Jul. 9, 2014.
Request for Continued Examination filed in U.S. Appl. No. 13/756,879. Aug. 28, 2014.
Non-Final Rejection issued in U.S. Appl. No. 14/080,595. Feb. 28, 2014.
Response After Non-Final Action filed in U.S. Appl. No. 14/080,595. May 28, 2014.
International Search Report and Written Opinion issued in PCT/US2014/028634. Aug. 27, 2014.
Final Rejection issued in U.S. Appl. No. 14/080,595. Sep. 3, 2014.

* cited by examiner

METHOD AND APPARATUS FOR DETECTING MOISTURE IN PORTABLE ELECTRONIC DEVICES

This application claims the benefit of U.S. Provisional Application No. 61/726,151, filed Nov. 14, 2012, the entirety of which is hereby incorporated herein by reference.

FIELD

The present invention deals with the field of devices and equipment generally used for determining the presence of dihydride monoxide (moisture or water) in enclosed portable electronic devices. The present invention provides a unique method and apparatus for the automatic detection of water in portable electronic devices, such as cell phones, digital music players, pagers, cameras, tablet computers and the like, after these units have been subjected to water, high-humidity conditions, or other unintended deleterious wetting agents that could render such devices inoperable. Such detection can be performed without any disassembly of the device required. At least one embodiment provides a user-controlled vacuum plenum that simultaneously scavenges air from within the portable electronic device while sampling the relative humidity to determine the level of water or moisture within the device. The relative humidity is sampled by a microcontroller and displayed on a user friendly interface to allow repair and retail shops to quickly determine whether the portable electronic device contains water or moisture within its enclosed interior.

BACKGROUND

Electronic devices are frequently manufactured using ultra-precision parts for tight fit-and-finish dimensions that are intended to keep moisture from entering the interior of the device. These electronic devices frequently have miniaturized solid-state transistorized memory for capturing and storing digitized media in the form of phone contact lists, e-mail addresses, digitized photographs, digitized music and the like. Many electronic devices are also manufactured to render disassembly by owners and or users difficult without rendering the device inoperable, even prior to drying attempts. With the continued miniaturization of electronics and increasingly powerful computerized software applications, it is commonplace for people today to carry multiple portable electronic devices. Cell phones are currently more ubiquitous than telephone land lines, and many people, on a daily basis throughout the world, inadvertently subject these devices to unintended contact with water. This occurs daily in the bathroom, kitchen, swimming pools, lakes, washing machines, or any other areas where various electronic devices can likely be submerged in water or subject to high-humid conditions.

SUMMARY

In the conventional art, difficulties currently exist in determining the level of moisture within an electronic device. Manufacturers commonly add "liquid contract indicators" (LCIs) to a portable electronic device; however, these are merely a visual indicator and fail to detect the severity of the moisture levels. With the advent of newer, more sophisticated and reliable methods to dry portable electronic devices, LCI's are essentially being rendered useless. Moreover, if a user can defeat the LCI visual indicator, then the repair or retail shop will not know whether the portable device is truly damaged from water, or whether the user has a valid warranty claim. Thus, a new type of moisture level detecting and indicating system is needed to allow individuals and repair shops to sample and determine the level of moisture within a portable electronic device without the need for disassembly.

Certain preferred features of the present invention address these and other needs and provide other important advantages. Embodiments of the present invention relate to equipment and methods for the vacuum scavenging of air from within the interior of a portable electronic device. More particularly, certain embodiments of the invention relate to an automatic vacuum that pulls entrapped air across a relative humidity sensor to determine the level of moisture within the electronics package.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein is not necessarily intended to address every object described herein, and each embodiment does not necessarily include each feature described. Other forms, embodiments, objects, advantages, benefits, features, and aspects of the present invention will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions or may have been created from scaled drawings. However, such dimensions, or the relative scaling within a figure, are by way of example only, and are not to be construed as limiting the scope of this invention.

DETAILED DESCRIPTION OF THE ILLUSTRATED EMBODIMENTS

Figure 1:
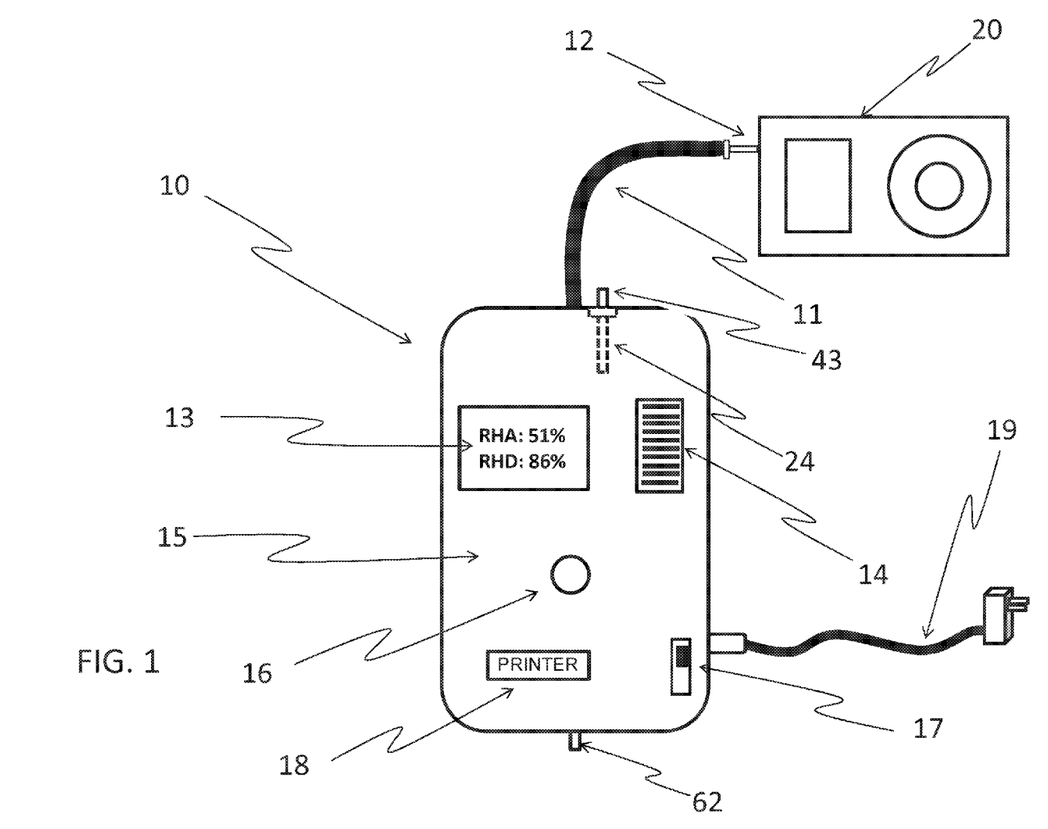
FIG. 1 is a top view diagram of a moisture sensing apparatus according to one embodiment of the present invention.

Referring first to FIG. 1, a top view diagram of a moisture sensing apparatus 10, e.g., an apparatus for determining the presence of dihydride monoxide (water), according to one embodiment of the present invention is shown. Moisture sensing apparatus 10 includes an enclosure 15, a display 13, a device under test ("DUT") air sampling tube 11, a DUT sampling port 12, a LED bar graph 14, a power switch 17, a test initiation and calibration button 16, an AC power adapter 19, a printer 18, ambient air sampling port or orifice 43 and vacuum pump exhaust port 62. The device 10 can also be battery powered and thereby rendered portable. Enclosure 15 is preferably fabricated of, for example, a known polymer plastic, glass, or metal, with suitable thickness and geometry to withstand handling by technicians or consumers. Most preferably, enclosure 15 is made from light weight ABS polymer plastic for strength and toughness in one preferred embodiment of this invention. In other embodiments of the invention, enclosure 15 can be made of elastomeric material to withstand handling from human oils and acids. DUT air sampling tube 11 is fabricated out of an elastomeric tube with minimum ID to attach to DUT sampling port 12. DUT sampling port 12 is fabricated out of a suitable material to prevent iron oxide (rust) build up from forming and coming in contact with moisture laden portable electronic devices. This material of construction can be a polymer, stainless steel, aluminum, or steel with a suitable coating.

Ambient air sampling port or orifice 43, which is substantially similar to DUT sampling port 12, is mounted through a wall of enclosure 15 for purposes of sampling ambient air. Ambient air sampling orifice 43 is pneumatically connected to pneumatic manifold 24 and serves as a pneumatic path for ambient air sampling, bringing ambient air into enclosure 15. Vacuum pump exhaust port 62 is also mounted through a wall of enclosure 15 for purposes of exhausting sampled air to atmosphere.

Figure 2:
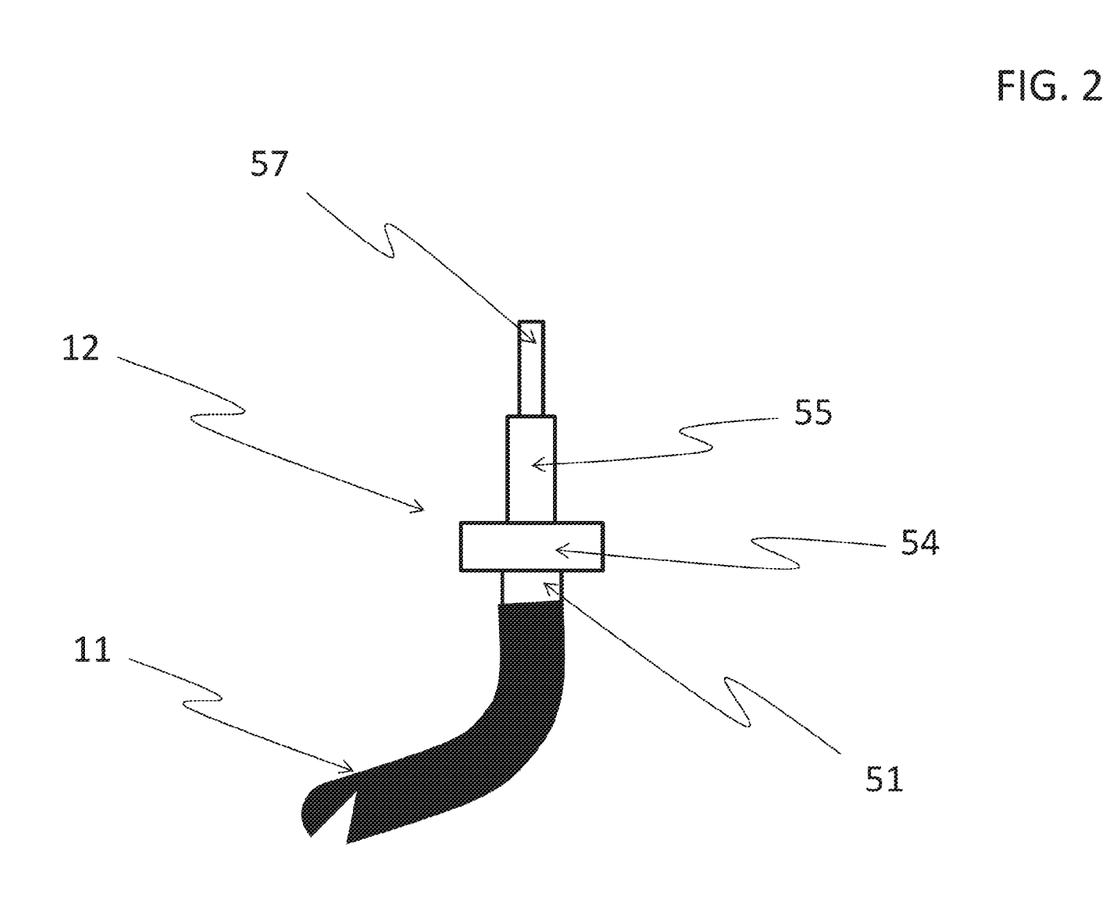
FIG. 2 is a side plan view of a sampling port according to one embodiment of the present invention.

Now referring to FIG. 2, a side plan view of DUT sampling port 12 is shown with a connected portion of DUT air sampling tube 11. DUT sampling port 12 is fabricated in such a manner that air sampling tube connector stub 51 is connected via an air-tight friction-fit engagement preferably inside DUT air sampling tube 11. DUT sampling port 12 is preferably molded or machined out of a solid, homogeneous piece of polymeric or metal material, and has an air sampling orifice disposed through the center of the entire length of the DUT sampling port 12 as best shown in FIG. 3.

Figure 3:
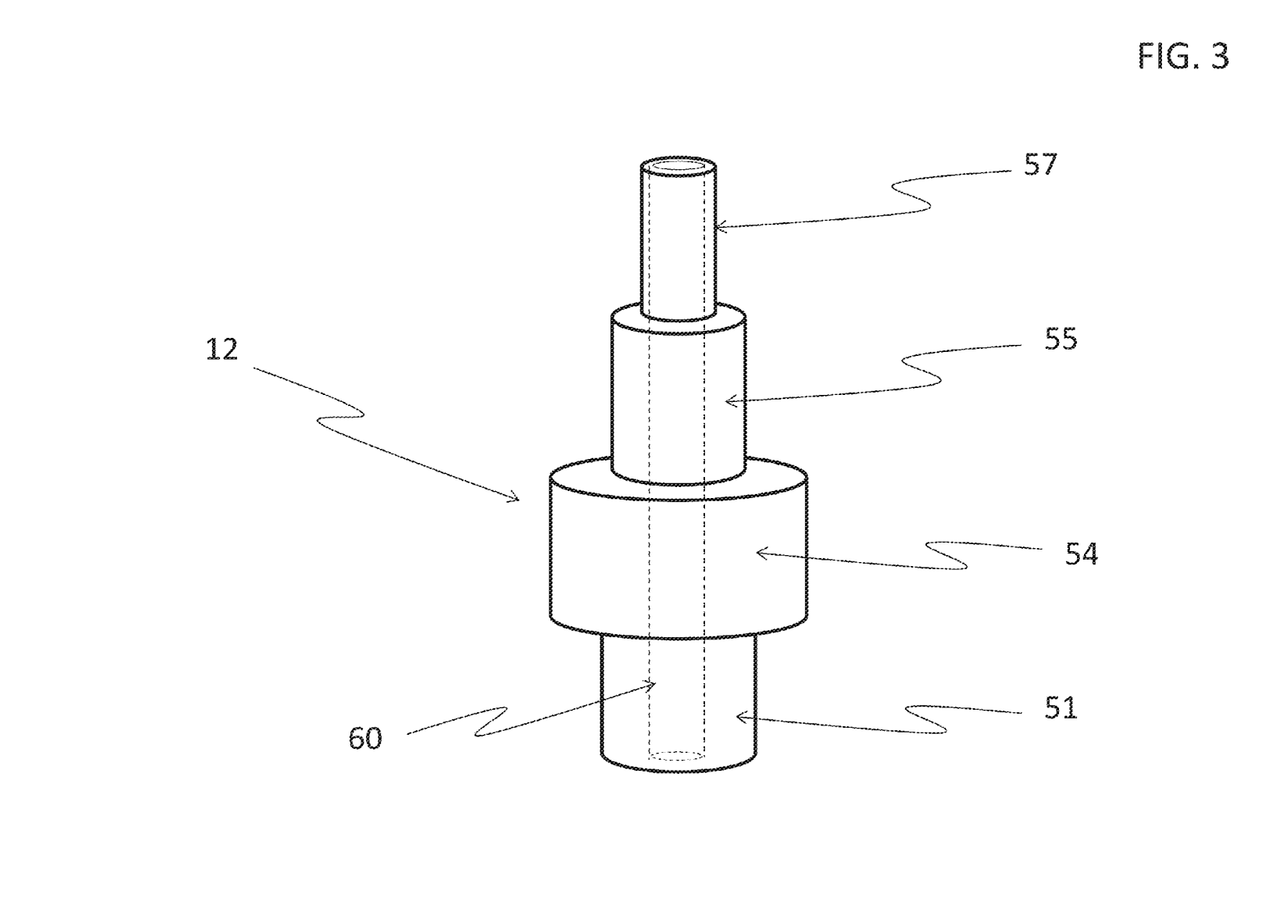
FIG. 3 is an isometric view of the sampling port depicted in FIG. 2.

FIG. 3 depicts the DUT sampling port 12 in an isometric view. DUT sampling port 12 is comprised of a body 54 providing the user with an enlarged means to better grip the DUT sampling port 12, an air sampling tube connector 51, a stepped sampling port comprised of smaller air sampling port 57, machined or molded in series with a larger air sampling port 55. Larger air sampling port 55 is molded or machined such that the entire air sampling port 12 is preferably made from a single, homogenous piece of material. Larger air sampling port 55 has a diameter that is the same as a standard 3.5 mm headphone jack for electronic devices, while smaller air sampling port 57 has a diameter that is the same as a standard 2.5 mm headphone jack. Air sampling orifice 60 is defined by a through-hole either molded or drilled running the entire length of DUT air sampling port 12. In other embodiments DUT air sampling port 12 can be fabricated from several pieces that are threaded and tapped together, or machined for a press fit. Such embodiments would provide similar usability; however, such parts would likely be cost prohibitive and subject to premature failure.

Although the invention preferably utilizes a standard headphone jack as an air sampling means on portable electronic devices, standard power connecters (mini USB and the like) utilized on various portable electronic devices could be utilized as air-sampling ports as well. While such other measurement or sampling points might be effective and useful, standard headphone jacks are typically provided as part of any electronic device and, therefore, are preferred for air sampling by the present invention.

Figure 4:
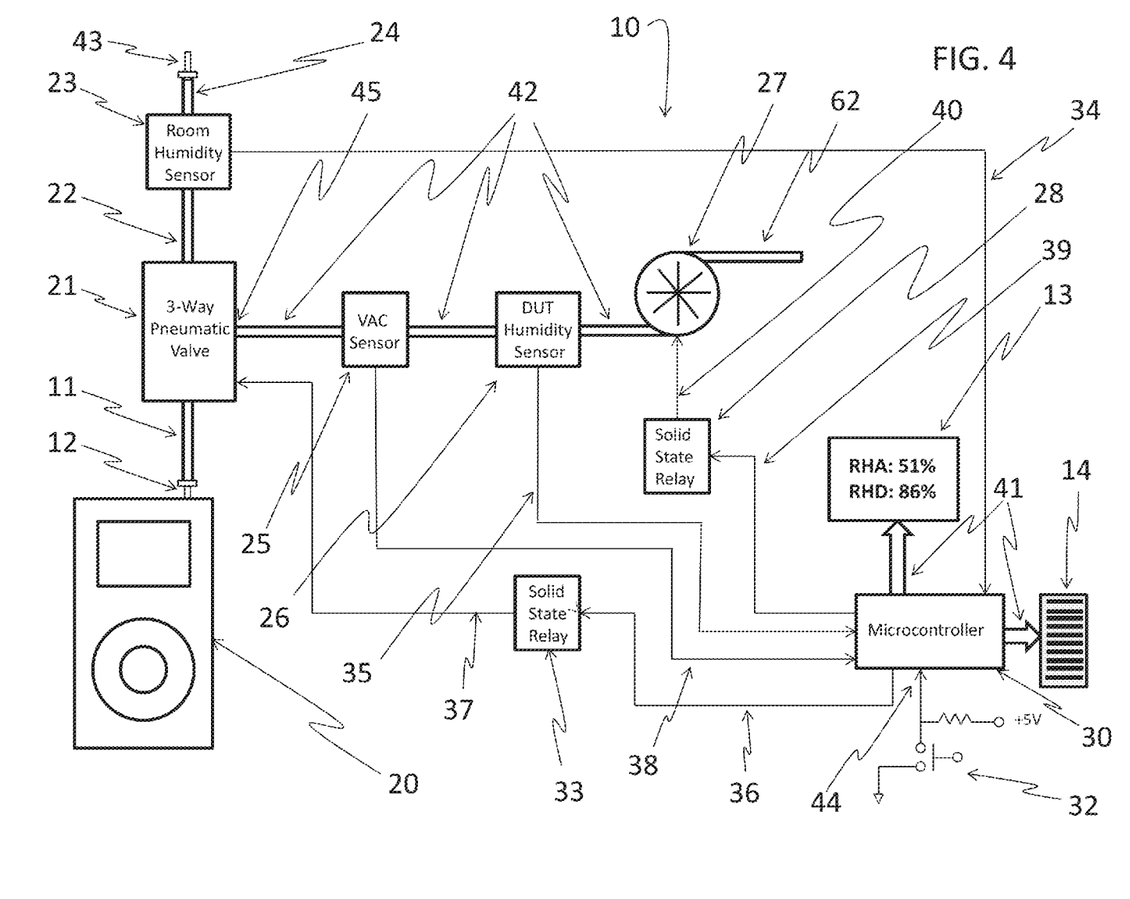
FIG. 4 is a block schematic diagram of an apparatus for determining the presence of dihydride monoxide in portable electronic devices according to one embodiment of the present invention.

Referring to now FIG. 4, an apparatus 10 for determining the presence of dihydride monoxide in portable electronic devices is shown in block schematic diagram according to one embodiment of the present invention. Apparatus 10 preferably includes a control microprocessor or microcontroller 30 electrically connected to character display 13 and LED bar graph 14 via data bus 41. Microcontroller 30 houses all software control code to display various messages and status indicia on character display 13 and drives LED bar graph 14 through output transistor drivers. Microcontroller 30 is also electrically connected to test button 16 through digital input 44. DUT 20 is pneumatically connected to 3-way pneumatic valve 21 via DUT sampling tube 11 and DUT sampling port 12. Valve 21 is actuated via 3-way driver signal 37 coming from pneumatic valve solid state relay 33, which is digitally switched via 3-way valve digital control signal 36 controlled by microcontroller 30.

Common pneumatic manifold 42 is pneumatically connected to 3-way valve 21 at the common pneumatic port 45. Manifold 42 serves to pneumatically connect 3-way pneumatic valve 21 to vacuum sensor 25, DUT relative humidity sensor 26 and vacuum pump 27. Vacuum sensor feedback signal 38 is electrically connected to microcontroller 30 and serves as means for microcontroller 30 to poll vacuum sensor 25 for calibration purposes. DUT humidity sensor feedback signal 35 is electrically connected to microcontroller 30 and provides means to sample relative humidity of DUT 20 during a test or to calibrate the system prior to operation. Vacuum pump digital control signal 39 is electrically connected from microcontroller 30 to vacuum pump solid state control relay 28, which controls the on-off operation of vacuum pump 27 via vacuum pump actuation signal 40. Room ambient relative humidity sensor 23 is connected to 3-way pneumatic valve 21 via calibration pneumatic manifold 22. Humidity sensor 23 is also connected to pneumatic manifold 24 and ambient sampling orifice 43, which has similar physical characteristics as that of DUT sampling port 12 as noted above. Humidity sensor 23 is electrically connected to microcontroller 30 via room ambient relative humidity feedback signal 34 and is used to determine room ambient relative humidity under control code housed in microcontroller 30.

Figure 5:
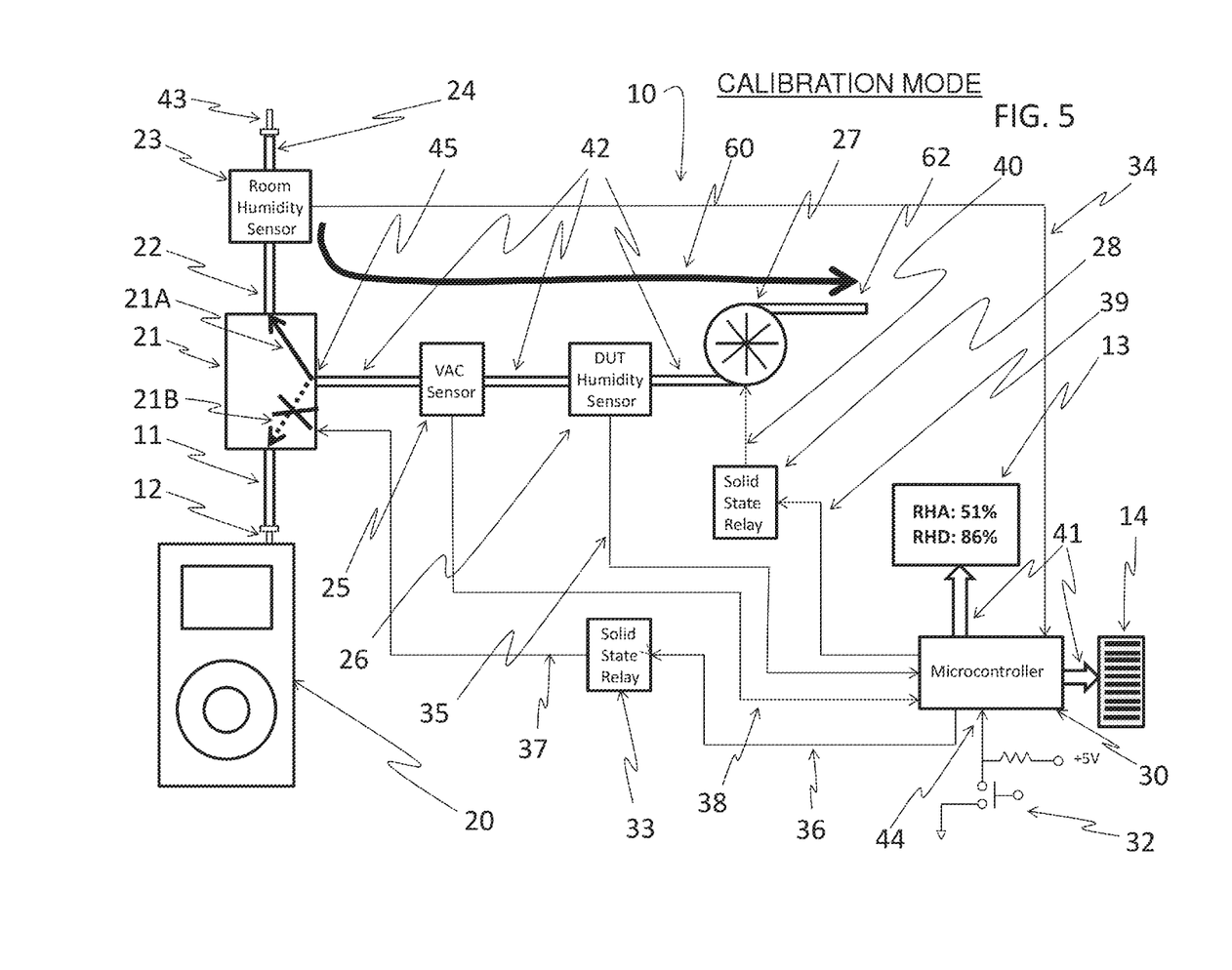
FIG. 5 depicts the moisture sensing apparatus of FIG. 4 in a calibration mode according to one embodiment of the present invention.

FIG. 5 depicts the moisture sensing apparatus 10, e.g., an apparatus for determining the presence of dihydride monoxide (water), in calibration mode. In calibration mode, 3-way pneumatic valve 21 is pneumatically switched such that air flows through room ambient pneumatic sampling circuit 21A and is blocked from entering DUT pneumatic sampling circuit 21B. Room ambient sampled airflow 60 is pulled by vacuum pump 27 through ambient sampling orifice 43, ambient relative humidity sensor 23, calibration pneumatic manifold 22, valve 21, common pneumatic manifold 42, vacuum sensor 25, and DUT humidity sensor 26. Vacuum pump exhaust port 62 is mounted through enclosure 15 and preferably disposed opposite that of DUT sampling port 12 and ambient air sampling orifice 43. Because the ambient air sampling orifice 43 and DUT sampling port 12 are preferably arranged on opposing ends of the apparatus 10 and, thus, not in proximity to the user's hand, no moisture from a his or her hand due to natural evaporation will affect the accuracy of the moisture sensing device.

Figure 6:
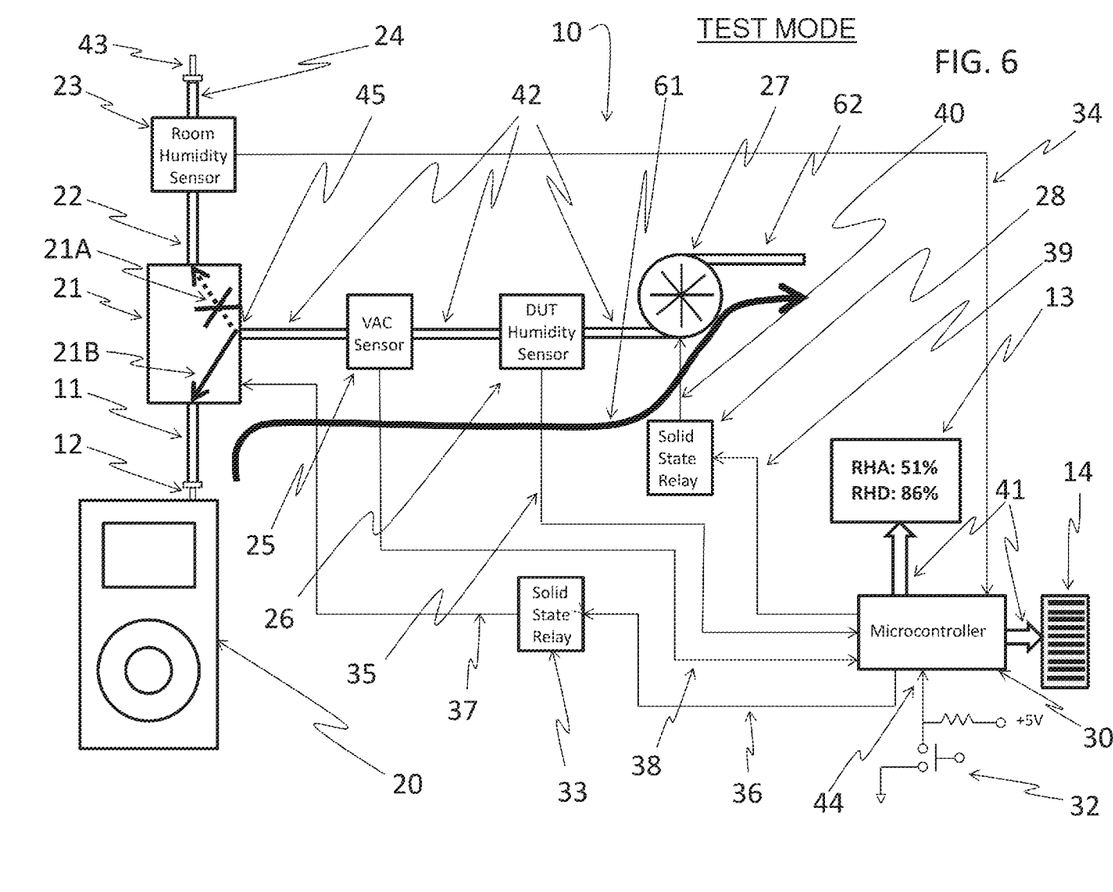
FIG. 6 depicts the moisture sensing apparatus of FIG. 4 in a moisture test mode according to one embodiment of the present invention.

FIG. 6 depicts the moisture sensing apparatus 10, in moisture test mode. In moisture test mode, 3-way pneumatic valve 21 is pneumatically switched such that air flows through DUT pneumatic sampling circuit 21B and is blocked from entering room ambient pneumatic sampling circuit 21A. DUT sampled airflow 61 is pulled by vacuum pump 27 through DUT 20, DUT sampling port 12, DUT air sampling tube 11, valve 21, common pneumatic manifold 42, vacuum sensor 25, and DUT relative humidity sensor 26.

In a preferred embodiment, microcontroller 30 control code initially invokes sampling routines to poll room ambient relative humidity sensor 23 via room ambient relative humidity feedback signal 34, vacuum sensor 25 via vacuum sensor feedback signal 38, and DUT relative humidity sensor 26 via DUT relative humidity feedback signal 35. Microcontroller 30 converts sensor signals so polled to digital character information and displays the ambient relative humidity and DUT relative humidity as ASCII characters on character display 13 by sending data and handshaking signals across electrical data bus 41. Such information may be displayed as, for example, "RHA" (Relative Humidity Atmosphere) and "RHD" (Relative Humidity Device) as shown in FIGS. 1 and 4-6. Nearly simultaneously, microcontroller 30 may convert DUT relative humidity feedback signal to a scaled 10-bit digital data signal and write this information to LED bar graph 14 via common data bus 41.

In one embodiment, the moisture sensing apparatus 10 provided by this invention operates as follows:

A portable electronic device that is suspected of "getting wet," has become wet, or is incipiently wet from exposure to high-humidity environments, is connected to DUT sampling port 12 via the DUT headphone jack provided as an integral part of the DUT 20. DUT sampling port 12 is pneumatically connected to DUT air sampling tube 11 and 3-way pneumatic valve 21. Power switch 17 is then turned to the "on" position, which provides electrical power to the device and its componentry. Microcontroller 30 is preferably provided with non-volatile memory in order to store software control code permanently. A user then presses test and calibration button 16 (FIG. 1), which is shown schematically as electrical switch 32 in FIGS. 4-6. Microcontroller 30 samples electrical switch signal 44 (FIG. 4) while simultaneously invoking a timer circuit to measure the length of time the electrical switch 16/32 is depressed. If the user holds the test and calibration button down for more than, for example, 1 second but less than 5 seconds, microcontroller 30 may determine the user desires to run an actual "test" routine in order to test for the presence of moisture in DUT 20. If the user holds the test and calibration button down for more than 5 seconds, for example, microcontroller 30 may determine the user desires instead to run the "calibration" routine. The times indicated herein are presented for illustration purposes only; anyone skilled in the art of microcontroller software control will understand such times can be easily modified to meet user preference. Any combinations or subcombinations of these times will provide the same desired effect of using one common push button to achieve either a calibration signal or a test signal being sent to microcontroller 30.

In the calibration mode, software routines in microcontroller 30 toggle 3-way driver signal 37 to logic 1, which energizes 3-way pneumatic valve solid state relay 33, switching 3-way pneumatic valve 21 into the calibration state, which in turn pneumatically blocks DUT pneumatic sampling circuit 21B and opens room ambient pneumatic sampling circuit 21A as shown in FIG. 5. Microcontroller 30 polls room ambient relative humidity sensor 23 via room ambient relative humidity feedback signal 34 and, nearly simultaneously, may poll vacuum sensor 25 via vacuum sensor feedback signal 38 and, using specific software conversion routines, establishes room ambient relative humidity with respect to the measured atmospheric pressure from vacuum sensor 25. These values are stored as variables under software control and used to establish a baseline room relative humidity as compared to vacuum pressure. Once these baseline values are determined, microcontroller 30 invokes software routines to display the room ambient relative humidity on character display 13 via signals sent electrically through data bus 41.

In this calibration mode, vacuum pump 27 is energized via vacuum pump actuation signal 40 derived from vacuum pump solid state control relay 28 and vacuum pump digital control signal 39 that is driven from microcontroller 30 under software control. Vacuum pump 27 starts and pulls air through common pneumatic manifold 42, DUT relative humidity sensor 26, vacuum sensor 25, and room ambient relative humidity sensor 23 via 3-way pneumatic valve 21, room ambient pneumatic manifold 22 and 24 and room ambient sampling orifice 43. A reduced vacuum pressure occurs in the pneumatic circuit with airflow 60 due to the restriction of room ambient sampling orifice 43 (which has a similar opening as DUT sampling port 12). Reduced vacuum pressure, which is sensed by microcontroller 30 via vacuum sensor 25 and vacuum sensor feedback signal 38, is sampled and stored as a vacuum pressure value and, nearly simultaneously, microcontroller 30 may sample room ambient relative humidity sensor 23 and also store that value via room ambient relative humidity feedback signal 34. These values are stored in memory within the microcontroller 30 and are used to provide a scaled correction factor as room ambient relative humidity sensor 23 and DUT relative humidity sensor 26 will provide a lower (false) reading with increased air flow from vacuum pump 27, which aids in mass transport evaporation. These vacuum pressure readings and resulting relative humidity readings are stored in microcontroller 30 as look-up variables, and provide a scaling mechanism for relative humidity adjustments due to the presence of reduced vacuum pressures as a result of airflow and passed through during the software test routine. As air is pulled across DUT humidity sensor 26 or ambient humidity sensor 23 via vacuum pump 27 (active situation), the resulting sensor response will be lower than if the same ambient humidity sensor 23 or DUT humidity sensor 26 were sampled with no air flow (static situation). This lower (false) reading is a result of air flowing over the humidity sensors and causing more rapid evaporation to occur by virtue of the air being passed across the sensors when vacuum pump 27 is in the powered state. Software algorithms correct for these false readings in the following way: microcontroller 30 samples the ambient relative humidity sensor 23 during the static situation with no airflow; microcontroller 30 then powers vacuum pump 27 in order to produce airflow across ambient humidity sensor 23 due to vacuum pump 27 evacuating and thereby pulling the air. This airflow is restricted by room air sampling orifice 43 and mimics the airflow restriction of DUT sampling port 12. Thus, an accurate correction factor can be computed in microcontroller 30 for ambient air humidity sensor 23 for various air flows that can be applied as a correction factor to DUT humidity sensor 26 due to similar airflows during the test cycle.

Now turning to the test mode as shown in FIG. 6, software routines in microcontroller 30 toggle 3-way driver signal 37 to logic 0, which de-energizes 3-way pneumatic valve solid state relay 33, switching 3-way pneumatic valve 21 into the test state, which in turn pneumatically opens DUT pneumatic sampling circuit 21B and blocks room ambient pneumatic sampling circuit 21A. (One of skill in the art will appreciate that the state of valve 21 (i.e., energized or de-energized) relative to being in either the calibration or test mode may be varied.) Microcontroller 30 polls DUT humidity sensor 26 via DUT relative humidity feedback signal 35 and, nearly simultaneously, may poll vacuum sensor 25 via vacuum sensor feedback signal 38 and, using specific software conversion routines, establish DUT relative humidity with respect to the measured atmospheric pressure from vacuum sensor 25. DUT relative humidity variable under software control is scaled using a linear interpolation of the vacuum pressure scaling factor derived from the calibration function. Once these scaled values are determined, microcontroller 30 invokes software routines to display the DUT relative humidity on character display 13 via signals sent electrically through data bus 41.

In this test mode, vacuum pump 27 is energized via vacuum pump actuation signal 40 derived from vacuum pump solid state control relay 28 and vacuum pump digital control signal 39 that is driven from microcontroller 30 under software control. Vacuum pump 27 starts and pulls air through common pneumatic manifold 42, DUT relative humidity sensor 26, vacuum sensor 25, air sampling tube 11, DUT sampling port 12, and DUT 20 via 3-way pneumatic valve 21. A reduced vacuum pressure occurs in the pneumatic circuit with airflow 61 due to the restriction of DUT sampling port 12. Reduced vacuum pressure, which is sensed by microcontroller 30 via vacuum sensor 25 and vacuum sensor feedback signal 38, is sampled and stored as a vacuum pressure value and, nearly simultaneously, DUT relative humidity sensor 26 may be sampled and that value also stored via DUT relative humidity feedback signal 35. These values are stored in memory and are mathematically scaled using the correction factors derived from the calibration routine. The scaled DUT relative humidity numerical result may then be electrically written across data bus 41 and displayed on character display 13 as the DUT relative humidity ("RHD").

Nearly simultaneously, microcontroller 30 may compute the difference of room ambient relative humidity and mathematically corrected DUT relative humidity, and that difference is used to create a look-up table in microcontroller 30. Microcontroller 30 provides electrical signals across data bus 41 and may also display a scaled difference on LED bar graph 14. Thus, the moisture sensing apparatus 10 determines the moisture level in a portable electronic device 20, and such data can be used for further diagnostic and/or repair purposes as desired.

We claim:

1. A moisture sensing apparatus comprising:
   a three-way pneumatic valve comprising a first port, a second port, and a third port;
   a room humidity sensor connected to the first port;
   a vacuum pressure sensor connected to the second port;
   a device under test (DUT) humidity sensor connected to the vacuum pressure sensor;
   an evacuation pump connected to the DUT humidity sensor;
   a sampling port and to a DUT;
   an air sampling orifice connected to the room humidity sensor;
   an exhaust port connected to the evacuation pump;
   a character display;
   a LED bar graph display; and
   a microprocessor controlled system to automatically control and calculate moisture levels.

2. The apparatus of claim 1, wherein said room ambient humidity sensor is used to determine room ambient moisture levels.

3. The apparatus of claim 1, wherein said DUT humidity sensor is used to determine moisture level in a portable electronic device.

4. The apparatus of claim 1, wherein said evacuation pump is used to pull air from room ambient air.

5. The apparatus of claim 1, wherein said three-way pneumatic valve is used to pneumatically switch out pneumatic sampling circuits.

6. The apparatus of claim 1, wherein said vacuum pressure sensor is used to determine vacuum pressure for mathematical scaling purposes.

7. The apparatus of claim 1, wherein said evacuation pump is used to pull air from inside a portable electronic device.

8. The apparatus of claim 1, wherein said sampling port is used to interface with a headphone jack of portable electronic devices to permit air sampling to occur.

9. The apparatus of claim 1, wherein said air sampling orifice restrictor is used to pneumatically mimic the standardized sampling port for correction factor calculations.

10. The apparatus of claim 1, wherein said evacuation pump is used to pull air from inside a portable electronic device.

11. The apparatus monoxide of claim 1, wherein said character display is used to display moisture levels of ambient air and air sampled in a portable electronic device.

12. The apparatus of claim 1, wherein said LED bar graph is used to graphically display relative difference of room ambient moisture and portable electronic device moisture from air sampled inside a portable electronic device.

13. The apparatus of claim 1, wherein said microprocessor is used to control electronic functionality.

14. The apparatus of claim 1, wherein said microprocessor is used to compute room ambient and device under test moisture levels.

15. The apparatus monoxide of claim 1, wherein said microprocessor is used to compute scaling factors for moisture levels in portable electronic devices.

16. The apparatus of claim 1, wherein said apparatus is portable.

17. The apparatus of claim 1, wherein said apparatus is rechargeable.

18. The apparatus of claim 1, further comprising a printer for providing a printed moisture level record.

19. The apparatus of claim 1, wherein exhaust port is located diametrically opposite and a minimum of 3 inches from that of the sampling port or the air sampling orifice.

20. The apparatus of claim 1, wherein said microprocessor automatically samples humidity sensors and computes a correction factor during active conditions.

21. The apparatus of claim 1, wherein the three-way pneumatic valve comprises a DUT pneumatic sampling circuit and a room ambient pneumatic sampling circuit, and wherein, in calibration mode, the three-way pneumatic valve is pneumatically switched such that air flows through the room ambient pneumatic sampling circuit and is blocked from entering the DUT pneumatic sampling circuit.

22. The apparatus of claim 1, wherein the three-way pneumatic valve comprises a DUT pneumatic sampling circuit and a room ambient pneumatic sampling circuit, and wherein, in test mode, the three-way pneumatic valve is pneumatically switched such that air flows through the DUT pneumatic sampling circuit and is blocked from entering the room ambient pneumatic sampling circuit.

* * * * *

UNITED STATES PATENT AND TRADEMARK OFFICE
CERTIFICATE OF CORRECTION

PATENT NO. : 9,488,565 B2  
APPLICATION NO. : 14/080705  
DATED : November 8, 2016  
INVENTOR(S) : Reuben Quincey Zielinski et al.

Page 1 of 1

It is certified that error appears in the above-identified patent and that said Letters Patent is hereby corrected as shown below:

In the Claims
Column 7, Line 65; after "a sampling port" insert -- connected to the third port --.
Column 8, Line 6; after "said room" delete "ambient".
Column 8, Line 28; after "orifice" delete "restrictor".
Column 8, Lines 28-29; delete "standardized".
Column 8, Line 46; delete "monoxide".

Signed and Sealed this
Eighteenth Day of April, 2017

Michelle K. Lee
*Director of the United States Patent and Trademark Office*